United States Patent
Famodu et al.

(10) Patent No.: US 6,630,617 B1
(45) Date of Patent: Oct. 7, 2003

(54) ENZYMES INVOLVED IN SQUALENE METABOLISM

(75) Inventors: Omolayo O. Famodu, Newark, DE (US); Anthony J. Kinney, Wilmington, DE (US); J. Antoni Rafalski, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/419,679

(22) Filed: Oct. 15, 1999

Related U.S. Application Data

(60) Provisional application No. 60/105,405, filed on Oct. 23, 1998.

(51) Int. Cl.[7] .......................... A01H 5/00; C12N 15/82; C07H 21/04
(52) U.S. Cl. ...................... 800/298; 536/23.6; 435/419; 435/468; 800/278
(58) Field of Search ...................... 536/23.6; 435/320.1, 435/419, 468; 800/290, 298, 278

(56) References Cited

PUBLICATIONS

Brenner; Errors in genome anniotation; 1999, Elsevier Science: 132–133.*
Smith et. al.; The challenges of genome sequence annotation or "The devil is in the details", 1997, Nature Biotechnology vol. 15:1222–1223.*
Doerks et.al.; Protein annotation: detective work for function prediction, 1998, Genetwork vol. 14, No. 6:248–250.*
Bairoch; Go hunting in sequence database but watch out for the traps, 1996, Genetwork:425–427.*
Schafer et.al.; An example of intron junctional sliding in the gene families encoding squalene monooxygene homologues in *Arabidopsis thaliana* and *Brassica napus*,1999, Plant Molecular Biology 39:721–728.*
NCBI General Identifier No. 5566676.
NCBI General Identifier No. 5468642.
NCBI General Identifier No. 5706248.
NCBI General Identifier No. 5608422.
NCBI General Identifier No. 5055959.
NCBI General Identifier No. 2309779.
NCBI General Identifier No. 2310417.
NCBI General Identifier No. 3107671.
NCBI General Identifier No. 702331.
NCBI General Identifier No. 4874404.
NCBI General Identifier No. 4589852.
NCBI General Identifier No. 2804728.
Morita et al., (1997), Biol. Pharm. Bull. 20:770–775.
Grieveson et al., (1997), Anal. Biochem. 252:19–23.

* cited by examiner

*Primary Examiner*—Elizabeth F. McElwain
*Assistant Examiner*—Stuart Baum

(57) ABSTRACT

This invention relates to an isolated nucleic acid fragment encoding a squalene metabolic enzyme. The invention also relates to the construction of a chimeric gene encoding all or a portion of the squalene metabolic enzyme, in sense or antisense orientation, wherein expression of the chimeric gene results in production of altered levels of the squalene metabolic enzyme in a transformed host cell.

13 Claims, No Drawings

SEQUENCE LISTING

<160> NUMBER OF SEQ ID NOS: 16

<210> SEQ ID NO 1
<211> LENGTH: 2558
<212> TYPE: DNA
<213> ORGANISM: Zea mays

<400> SEQUENCE: 1

```
gcacgagcaa gcacagcgcc gacctcctca tgcgcatcca gttcgccaaa gaaaactcga      60
ttgagcttca ccttccaggc atcaagctcg gtgagcatga agatgtgacc gaggaagctg     120
tgttgactac attgaaaagg gcaatcagcc gtttctctac tctccaggca catgatggac     180
actggcctgg ggattatggt ggtcctatgt tccttatgcc aggcttgatc ataacattgt     240
atgtgactgg agcactaaac actgtcttgt cattggaaca ccagaaggag atccgccggt     300
atctttataa tcaccagaat gaagatggcg gctggggctt gcacattgag ggtccaagca     360
ccatgttcgg ctcagcactg acctatgtta ttttgagatt gcttggagag ggaccagata     420
gtggagatgg agccatggag aaaggtcgaa actggatatt agaccatggt ggagcaacat     480
atataacatc gtgggggaag ttttggcttt cggtactagg tgtatttgaa tggtctggta     540 acaaccggt gccaccagaa gtatggctac tgccatatct cctcccattt cacccaggga     600
ggatgtggtg tcattgtcga atggtgtatt tgccaatgtg ctacatttat gggaagaggt     660
ttgttggccg aatcacacca cttctgttgg aattaaggaa ggaacttttc aaagaccctt     720
acagcaagat tgattgggac aaggcccgca acctatgtgc caaggaagat ctgtactacc     780
cacacccatt cgttcaagat gtgttgtggg ccactctcca taaattcgtt gaaccagtta     840
```

-continued

```
tgatgcattg gcctggcagc aaattgaggg agaaagctct ggaaacagtc atgcaacatg    900
ttcattatga agatgagaac actcgttata tttgcattgg tcctgtaaac aaggtattga    960
atatgcttgc ttgctggatt gaagatccaa actcggaggc cttcaaactt catatcccac   1020
gagtctatga ttacttgtgg cttgctgaag atggcatgaa gatgcagggt tataatggca   1080
gccaactttg ggatacagct ttcacagttc aagccattgt ggctaccaac cttattgaag   1140
agtttggtcc taccettaaa ctagcacaca actatatcaa gaattcacag gttcttgatg   1200
actgccctgt tgatctgaat gactggtacc gccacacatc taaaggtgca tggccattct   1260
caactgctga tcatggttgg cctatatctg attgcactgc tgaaggacta aaggcttcat   1320
tattgttatc aaggatctct cccaaaattg ttggtgaacc gatggaagct aatagatttt   1380
atgatgctgt cagttgtctg atgtcttata tgaatgataa tggcggtttc gcgacatatg   1440
aactcacaag atcttatccc tggttggagc tgatcaatcc cgctgagacc tttggggata   1500
ttgtgattga ttaccegtat gttgaatgta catcagcagc aattcaggcc ctgacatcat   1560
tcaaaaaact atacctggg caccgcagga agaggtgga taactgtatc agcaaagctt    1620
ccaatttcat cgagagtatt cagaaaagcg atggttcatg gtatggctct tgggccgtct   1680
gtttcacata cggcacttgg tttggtgtga agggactaat tgctgctggt agaacatttg   1740
agaacagtcc tgcaattaga aaggcatgcg actttctgtt gtcaaaagaa cttccttccg   1800
gtggttgggg agaaagctat ttgtcatctc aagaccaggt ttacaccaat ctcaaaggca   1860
accggcctca tgcggtgaac actagttggg ccatgctggc gctgattgat gcgggccagg   1920
ccgagagaga tccaacgcct ctacaccgag cagcaaaggt tttgatcaac ttacaatcag   1980
aggacggaga atttcctcag caagagatca taggagtgtt caacaagaac tgcatgataa   2040
gctactccca gtacaggaac atcttcccga tttgggctct gggtgagtac cggtgtcgag   2100
tcttgggggc tggcaagcct tggcggtgaa cgggaggtgt gtgtgtgtgt gtgtcatgga   2160
tcagcttttg tgagtagcca tgtggaagtt ggaataatgt agctacgtta cgttcagggg   2220
gttgcgttac tagtggtcct agtaataata gtgatggtga tagtaatgta ctcctcatta   2280
ttacaatctc aaagcggttc atgccattgc catgcacatc tcagatccga gtcacgcact   2340
tgagagagtt caaggattgc aagtatagtt gggagaatca aatccaatcg gcttattgtc   2400
tgctcatctc aggtgtcagg tctttcagcc acacacacat acacataccc tgacctagag   2460
attttttgcca ttatgaaaca ttacatgttc ggcttcgttg aaatgaagat gagaagggat   2520
tcgacgaaaa aaaaaaaaaa aaaaaaaaa aaaaaaaa                           2558
```

<210> SEQ ID NO 2
<211> LENGTH: 701
<212> TYPE: PRT
<213> ORGANISM: Zea mays

<400> SEQUENCE: 2

Thr Ser Lys His Ser Ala Asp Leu Leu Met Arg Ile Gln Phe Ala Lys
 1               5                  10                  15

Glu Asn Ser Ile Glu Leu His Leu Pro Gly Ile Lys Leu Gly Glu His
            20                  25                  30

Glu Asp Val Thr Glu Glu Ala Val Leu Thr Thr Leu Lys Arg Ala Ile
        35                  40                  45

Ser Arg Phe Ser Thr Leu Gln Ala His Asp Gly His Trp Pro Gly Asp
    50                  55                  60

Tyr Gly Gly Pro Met Phe Leu Met Pro Gly Leu Ile Ile Thr Leu Tyr

-continued

```
             65                  70                  75                  80
Val Thr Gly Ala Leu Asn Thr Val Leu Ser Leu Glu His Gln Lys Glu
                 85                  90                  95
Ile Arg Arg Tyr Leu Tyr Asn His Gln Asn Glu Asp Gly Gly Trp Gly
                100                 105                 110
Leu His Ile Glu Gly Pro Ser Thr Met Phe Gly Ser Ala Leu Thr Tyr
                115                 120                 125
Val Ile Leu Arg Leu Leu Gly Glu Gly Pro Asp Ser Gly Asp Gly Ala
            130                 135                 140
Met Glu Lys Gly Arg Asn Trp Ile Leu Asp His Gly Gly Ala Thr Tyr
145                 150                 155                 160
Ile Thr Ser Trp Gly Lys Phe Trp Leu Ser Val Leu Gly Val Phe Glu
                165                 170                 175
Trp Ser Gly Asn Asn Pro Val Pro Pro Glu Val Trp Leu Leu Pro Tyr
                180                 185                 190
Leu Leu Pro Phe His Pro Gly Arg Met Trp Cys His Cys Arg Met Val
            195                 200                 205
Tyr Leu Pro Met Cys Tyr Ile Tyr Gly Lys Arg Phe Val Gly Arg Ile
210                 215                 220
Thr Pro Leu Leu Leu Glu Leu Arg Lys Glu Leu Phe Lys Asp Pro Tyr
225                 230                 235                 240
Ser Lys Ile Asp Trp Asp Lys Ala Arg Asn Leu Cys Ala Lys Glu Asp
                245                 250                 255
Leu Tyr Tyr Pro His Pro Phe Val Gln Asp Val Leu Trp Ala Thr Leu
                260                 265                 270
His Lys Phe Val Glu Pro Val Met Met His Trp Pro Gly Ser Lys Leu
            275                 280                 285
Arg Glu Lys Ala Leu Glu Thr Val Met Gln His Val His Tyr Glu Asp
            290                 295                 300
Glu Asn Thr Arg Tyr Ile Cys Ile Gly Pro Val Asn Lys Val Leu Asn
305                 310                 315                 320
Met Leu Ala Cys Trp Ile Glu Asp Pro Asn Ser Glu Ala Phe Lys Leu
                325                 330                 335
His Ile Pro Arg Val Tyr Asp Tyr Leu Trp Leu Ala Glu Asp Gly Met
            340                 345                 350
Lys Met Gln Gly Tyr Asn Gly Ser Gln Leu Trp Asp Thr Ala Phe Thr
            355                 360                 365
Val Gln Ala Ile Val Ala Thr Asn Leu Ile Glu Glu Phe Gly Pro Thr
            370                 375                 380
Leu Lys Leu Ala His Asn Tyr Ile Lys Asn Ser Gln Val Leu Asp Asp
385                 390                 395                 400
Cys Pro Gly Asp Leu Asn Asp Trp Tyr Arg His Thr Ser Lys Gly Ala
                405                 410                 415
Trp Pro Phe Ser Thr Ala Asp His Gly Trp Pro Ile Ser Asp Cys Thr
                420                 425                 430
Ala Glu Gly Leu Lys Ala Ser Leu Leu Leu Ser Arg Ile Ser Pro Lys
            435                 440                 445
Ile Val Gly Glu Pro Met Glu Ala Asn Arg Phe Tyr Asp Ala Val Ser
            450                 455                 460
Cys Leu Met Ser Tyr Met Asn Asp Asn Gly Gly Phe Ala Thr Tyr Glu
465                 470                 475                 480
Leu Thr Arg Ser Tyr Pro Trp Leu Glu Leu Ile Asn Pro Ala Glu Thr
                485                 490                 495
```

Phe Gly Asp Ile Val Ile Asp Tyr Pro Tyr Val Glu Cys Thr Ser Ala
            500                 505                 510

Ala Ile Gln Ala Leu Thr Ser Phe Lys Lys Leu Tyr Pro Gly His Arg
        515                 520                 525

Arg Lys Glu Val Asp Asn Cys Ile Ser Lys Ala Ser Asn Phe Ile Glu
    530                 535                 540

Ser Ile Gln Lys Ser Asp Gly Ser Trp Tyr Gly Ser Trp Ala Val Cys
545                 550                 555                 560

Phe Thr Tyr Gly Thr Trp Phe Gly Val Lys Gly Leu Ile Ala Ala Gly
                565                 570                 575

Arg Thr Phe Glu Asn Ser Pro Ala Ile Arg Lys Ala Cys Asp Phe Leu
            580                 585                 590

Leu Ser Lys Glu Leu Pro Ser Gly Gly Trp Gly Glu Ser Tyr Leu Ser
        595                 600                 605

Ser Gln Asp Gln Val Tyr Thr Asn Leu Lys Gly Asn Arg Pro His Ala
    610                 615                 620

Val Asn Thr Ser Trp Ala Met Leu Ala Leu Ile Asp Ala Gly Gln Ala
625                 630                 635                 640

Glu Arg Asp Pro Thr Pro Leu His Arg Ala Ala Lys Val Leu Ile Asn
                645                 650                 655

Leu Gln Ser Glu Asp Gly Glu Phe Pro Gln Gln Glu Ile Ile Gly Val
            660                 665                 670

Phe Asn Lys Asn Cys Met Ile Ser Tyr Ser Gln Tyr Arg Asn Ile Phe
        675                 680                 685

Pro Ile Trp Ala Leu Gly Glu Tyr Arg Cys Arg Val Leu
    690                 695                 700

<210> SEQ ID NO 3
<211> LENGTH: 1882
<212> TYPE: DNA
<213> ORGANISM: Oryza sativa

<400> SEQUENCE: 3
gcacgagatc actgctttcg gtgcttggtg tatttgactg gtctggcaac aacccagtgc     60
caccagaaat atggttgttg ccatatttcc tgccgattca tccagggcga atgtggtgtc    120
attgccggat ggtttatttg cctatgtgtt acatttatgg aaagaggttt gtgggcccag    180
ttacaccaat tatattggaa ttaagaaagg aactctacga agtaccctac aatgaagttg    240
attgggacaa ggctcgcaat ctatgtgcta aggaagatct gtactatcca catccattcg    300
tgcaggatgt attatgggcc actctccaca aatttgttga accagctatg ttgcgttggc    360
ctgggaacaa attgagggag aaagctttgg acactgtcat gcagcatatt cattatgaag    420
atgagaacac ccgatatatt tgcattggtc agtaaaacaa ggtattaaat atgcttgctt    480
gctggattga agatccaaac tcagaggcat tcaaactcca cattccaaga gtccacgatt    540
acctatggat tgcagaagat ggcatgaaaa tgcagggtta atgaagc cagctgtggg      600 acacagcttt cacagttcaa gctatagtgg ctactggcct cattgaagaa tttggtccta    660
ctcttaaact agcacatggc tacataaaga aaacgcaggt tatcgatgac tgccctggag    720
atcttagtca gtggtaccgc cacatatcta aggtgcatg gccctttttct actgctgatc    780 atggttggcc tatatcagat tgcactgcag aaggacttaa ggcggcatta ttgctatcga    840
agatttctcc agatattgtt ggcgaagcag tggaagttaa tagactgtat gattctgtca    900
attgtttgat gtcatacatg aatgataatg gtggatttgc aacatatgaa ctcacaaggt    960

-continued

```
cttatgcctg gctggagctt atcaatcctg ctgagacctt tggggacatt gtgattgatt    1020
atccttatgt ggaatgcact tcagcagcaa ttcaggccct gacagcattt aaaaagctct    1080
accctggaca ccgcaagagt gaaatagaca actgtataag caaagctgct agctttattg    1140
agggtattca aaaagcgat ggttcatggt atggttcttg gctgttttgt tttacctatg     1200
gcacatggtt tggtgtaaag ggattagttg ctgctggtag acattcaaa aacagtcctg     1260 caatcagaaa ggcatgtgac tttttgttgt caaaagagct tccttctgga ggctggggag    1320
aaagctattt gtcatcccaa gatcaggttt ataccaatct cgaagggaag cgacctcatg    1380
cggtgaacac tggttgggcc atgctagccc taatcgatgc agggcaggct gagagagatc    1440
caattccttt gcatcgagca gcgaaggttt tgatcaactt acaatcggaa gatggtgaat    1500
ttccccagca agagatcatt ggagtcttca acaaaaactg catgatcagc tactccgagt    1560
atagaaacat cttccctatt tgggcccttg gggagtaccg tcgccgcgtc ttggccgcag    1620
acaagtagtt cagcacgagc agagcagcag caccaacaat gtgcatgtat ttatacgtga    1680
aataatgtag ctatgtttca gttgtaataa tgtggctata tgtattctcc cgttagtgat    1740
gccacgcgag cgtagtcaaa tagaaacgca ttttgacaca agttcgagat gaatggattc    1800
ctgaatcgaa tgtttgtgtt caaaaaaaaa aaaaaaaaa aaaaaaaaaa aaaaaaaaa     1860 aaaaaaaaaa aaaaaaaaaa cc                                           1882
```

<210> SEQ ID NO 4
<211> LENGTH: 541
<212> TYPE: PRT
<213> ORGANISM: Oryza sativa

<400> SEQUENCE: 4

```
Thr Arg Ser Leu Leu Ser Val Leu Gly Val Phe Asp Trp Ser Gly Asn
  1               5                  10                  15

Asn Pro Val Pro Pro Glu Ile Trp Leu Leu Pro Tyr Phe Leu Pro Ile
                 20                  25                  30

His Pro Gly Arg Met Trp Cys His Cys Arg Met Val Tyr Leu Pro Met
             35                  40                  45

Cys Tyr Ile Tyr Gly Lys Arg Phe Val Gly Pro Val Thr Pro Ile Ile
         50                  55                  60

Leu Glu Leu Arg Lys Glu Leu Tyr Glu Val Pro Tyr Asn Glu Val Asp
 65                  70                  75                  80

Trp Asp Lys Ala Arg Asn Leu Cys Ala Lys Glu Asp Leu Tyr Tyr Pro
                 85                  90                  95

His Pro Phe Val Gln Asp Val Leu Trp Ala Thr Leu His Lys Phe Val
            100                 105                 110

Glu Pro Ala Met Leu Arg Trp Pro Gly Asn Lys Leu Arg Glu Lys Ala
        115                 120                 125

Leu Asp Thr Val Met Gln His Ile His Tyr Glu Asp Glu Asn Thr Arg
130                 135                 140

Tyr Ile Cys Ile Gly Pro Val Asn Lys Val Leu Asn Met Leu Ala Cys
145                 150                 155                 160

Trp Ile Glu Asp Pro Asn Ser Glu Ala Phe Lys Leu His Ile Pro Arg
                165                 170                 175

Val His Asp Tyr Leu Trp Ile Ala Glu Asp Gly Met Lys Met Gln Gly
            180                 185                 190

Tyr Asn Gly Ser Gln Leu Trp Asp Thr Ala Phe Thr Val Gln Ala Ile
        195                 200                 205
```

```
Val Ala Thr Gly Leu Ile Glu Glu Phe Gly Pro Thr Leu Lys Leu Ala
    210                 215                 220

His Gly Tyr Ile Lys Lys Thr Gln Val Ile Asp Asp Cys Pro Gly Asp
225                 230                 235                 240

Leu Ser Gln Trp Tyr Arg His Ile Ser Lys Gly Ala Trp Pro Phe Ser
                245                 250                 255

Thr Ala Asp His Gly Trp Pro Ile Ser Asp Cys Thr Ala Glu Gly Leu
                260                 265                 270

Lys Ala Ala Leu Leu Ser Lys Ile Ser Pro Asp Ile Val Gly Glu
275                 280                 285

Ala Val Glu Val Asn Arg Leu Tyr Asp Ser Val Asn Cys Leu Met Ser
    290                 295                 300

Tyr Met Asn Asp Asn Gly Gly Phe Ala Thr Tyr Glu Leu Thr Arg Ser
305                 310                 315                 320

Tyr Ala Trp Leu Glu Leu Ile Asn Pro Ala Glu Thr Phe Gly Asp Ile
                325                 330                 335

Val Ile Asp Tyr Pro Tyr Val Glu Cys Thr Ser Ala Ala Ile Gln Ala
                340                 345                 350

Leu Thr Ala Phe Lys Lys Leu Tyr Pro Gly His Arg Lys Ser Glu Ile
                355                 360                 365

Asp Asn Cys Ile Ser Lys Ala Ala Ser Phe Ile Glu Gly Ile Gln Lys
370                 375                 380

Ser Asp Gly Ser Trp Tyr Gly Ser Trp Ala Val Cys Phe Thr Tyr Gly
385                 390                 395                 400

Thr Trp Phe Gly Val Lys Gly Leu Val Ala Ala Gly Arg Thr Phe Lys
                405                 410                 415

Asn Ser Pro Ala Ile Arg Lys Ala Cys Asp Phe Leu Leu Ser Lys Glu
                420                 425                 430

Leu Pro Ser Gly Gly Trp Gly Glu Ser Tyr Leu Ser Ser Gln Asp Gln
                435                 440                 445

Val Tyr Thr Asn Leu Glu Gly Lys Arg Pro His Ala Val Asn Thr Gly
    450                 455                 460

Trp Ala Met Leu Ala Leu Ile Asp Ala Gly Gln Ala Glu Arg Asp Pro
465                 470                 475                 480

Ile Pro Leu His Arg Ala Ala Lys Val Leu Ile Asn Leu Gln Ser Glu
                485                 490                 495

Asp Gly Glu Phe Pro Gln Gln Glu Ile Ile Gly Val Phe Asn Lys Asn
                500                 505                 510

Cys Met Ile Ser Tyr Ser Glu Tyr Arg Asn Ile Phe Pro Ile Trp Ala
                515                 520                 525

Leu Gly Glu Tyr Arg Arg Arg Val Leu Ala Ala Asp Lys
    530                 535                 540

<210> SEQ ID NO 5
<211> LENGTH: 2560
<212> TYPE: DNA
<213> ORGANISM: Glycine max

<400> SEQUENCE: 5
ttggcctctt gccagcaaaa cagaatgtgg aagctcaagt tcgccgaagg agggaatcca      60
tggcttcgga cattgaacaa tcacgttgga agacaggtgt gggagttcga tcctaagctt     120
ggatcgccgc aagatctcct cgagattgag aaagctcgcc agaattttca cgataaccgc     180
tttacccaca acacagcgc tgatctactt atgcggatgc agttcgcaag agagaaccca      240
```

-continued

```
acacgtgaag tcttgcccaa agtcggagtt aaggatattg aggatgtgac ccaagagatt    300
gtgacaaaaa cattaagaag ggccgtaagt ttccattcaa ctctccagtg ccatgacgga    360
cactggccgg gagattatgg aggtcccatg tttctgatgc ctggcttggt aattactctg    420
tctatcactg gggcgttgaa tacagtctta actgaagaac atagaaagga aatatgccgt    480
tacctctata atcatcaaaa caaggatggt gggtgggtt  tgcatattga aggtccaagc    540
accatgtttg gctctgtctt gagttatatt actctgagat tgctaggtga ggggcctaat    600
gatggacaag gggaaatgga gaaggcacgt gactggattc tagggcatgg tggtgctact    660
tatataacgt catgggggaa gatgtggctt tcagtacttg gagtgtatga atggtctgga    720
aataatcccc tgcccctga  gatatggctc cttccataca tgcttccatt tcatccagga    780
aggatgtggt gtcactgccg gatggtctat ttgccgatgt cctacttata tggcaagagg    840
tttgttggtc caatctcacc aacagtatta tctttgagaa aagagcttta tacagtacca    900
taccatgata tagattggga tcaggctcgc aatttgtgtg caaggaagaa tttgtactat    960
cctcacccac ttgtacagga tattctttgg gcatctctac acaagttcct tgagcctatt   1020
ctgatgcatt ggcctggaaa agattgagg  gaaaaggcta ttatttctgc attggagcat   1080
atacattacg aagatgagaa tactcgatat atttgcatag gtcctgtaaa taaggtgtta   1140
aatatgcttt gctgttgggt ggaagatcca aattctgagg ccttcaagtt gcatcttccc   1200
aggatttatg attatctatg gattgcagaa gatggcatga aaatgcaggg ctacaatgga   1260
agtcaactat gggacactgc ttttgctgtc caagcaatta ttgcatctaa cctcattgaa   1320
gaatttggtc aactataag  aaaagctcat acctatatta agaattcaca ggttttagaa   1380
gattgtccag gtgatcttaa taaatggtac cgtcacattt caaaggtgc  ttggccttt    1440
tcaactggag atcatggatg gccaatttct gactgcacag ctgaaggact gaaagctgtt   1500
ctattactat ccaaaattgc accagaaata gttggtgagc aatagacgt  gaagcgatta   1560
tatgattctg taaatgtcat tctctcacta cagaatgaag atggtggttt tgcaacatat   1620
gagcttaaac gatcttataa ttggttggag ataatcaatc ctgctgaaac ttttggtgac   1680
atcgttattg attatcctta tgtggaatgt acatcagcag cgattcaagc tttggcatca   1740
tttaggaaat tatatcctgg gcatcgccga gaagaaatac aacattgtat cgataaagcc   1800
actaccttca ttgaaaaaat acaagcttca gatggatcat ggtatggttc ttggggagtt   1860
tgcttcactt acggtgcttg gtttggggta aaaggtctga ttgctgctgg aaggagtttc   1920
agtaattgct caagcatccg taaagcttgt gaatttctgc tgtccaagca gcttccttct   1980
ggtggctggg gagagagtta tctgtcctgt caaaacaagg tgtattcaaa tctggaaggc   2040
aacaggtctc atgtggtcaa cactgggtgg gctatgttgg ctctcattga tgctggacag   2100
gctaagagag attcgcaacc actgcaccgg gcagctgcat acttgataaa ttcccaattg   2160
gaggacggtg actttccgca gcaggaaata atgggagtct caacaagaa  ttgcatgatc   2220
acatacgccg catacagaaa catattcccc atttgggcgt tgggagaata ccaatcccaa   2280
gtattgcaat ctcgttaatc gagccttagt tagggtgtca tcctaattat ttcgacctgt   2340
ggacagtaaa agaaataata ataataacct attttttctt tatttccatg gctctcttaa   2400
aatgtttgtg actaatgagt ttagtagtca gctaaaaaaa aaagcaaaca cgtggagaat   2460
gcctgtaagt ttttctatt  actcatagac gcctctcttg ctttccctgc agcagaggaa   2520
ttaaatatat acataaatag agatataaaa aaaaaaaaa                          2560
```

```
<210> SEQ ID NO 6
<211> LENGTH: 757
<212> TYPE: PRT
<213> ORGANISM: Glycine max

<400> SEQUENCE: 6
```

| | | | | | | | | | | | | | | |
|---|---|---|---|---|---|---|---|---|---|---|---|---|---|---|
| Met | Trp | Lys | Leu | Lys | Phe | Ala | Glu | Gly | Gly | Asn | Pro | Trp | Leu | Arg | Thr |
| 1 | | | | 5 | | | | | 10 | | | | | 15 | |
| Leu | Asn | Asn | His | Val | Gly | Arg | Gln | Val | Trp | Glu | Phe | Asp | Pro | Lys | Leu |
| | | | 20 | | | | | 25 | | | | | 30 | | |
| Gly | Ser | Pro | Gln | Asp | Leu | Leu | Glu | Ile | Glu | Lys | Ala | Arg | Gln | Asn | Phe |
| | | 35 | | | | | 40 | | | | | 45 | | | |
| His | Asp | Asn | Arg | Phe | Thr | His | Lys | His | Ser | Ala | Asp | Leu | Leu | Met | Arg |
| | 50 | | | | | 55 | | | | | 60 | | | | |
| Met | Gln | Phe | Ala | Arg | Glu | Asn | Pro | Thr | Arg | Glu | Val | Leu | Pro | Lys | Val |
| 65 | | | | | 70 | | | | | 75 | | | | | 80 |
| Gly | Val | Lys | Asp | Ile | Glu | Asp | Val | Thr | Gln | Glu | Ile | Val | Thr | Lys | Thr |
| | | | | 85 | | | | | 90 | | | | | 95 | |
| Leu | Arg | Arg | Ala | Val | Ser | Phe | His | Ser | Thr | Leu | Gln | Cys | His | Asp | Gly |
| | | | 100 | | | | | 105 | | | | | 110 | | |
| His | Trp | Pro | Gly | Asp | Tyr | Gly | Gly | Pro | Met | Phe | Leu | Met | Pro | Gly | Leu |
| | | 115 | | | | | 120 | | | | | 125 | | | |
| Val | Ile | Thr | Leu | Ser | Ile | Thr | Gly | Ala | Leu | Asn | Thr | Val | Leu | Thr | Glu |
| | 130 | | | | | 135 | | | | | 140 | | | | |
| Glu | His | Arg | Lys | Glu | Ile | Cys | Arg | Tyr | Leu | Tyr | Asn | His | Gln | Asn | Lys |
| 145 | | | | | 150 | | | | | 155 | | | | | 160 |
| Asp | Gly | Gly | Trp | Gly | Leu | His | Ile | Glu | Gly | Pro | Ser | Thr | Met | Phe | Gly |
| | | | | 165 | | | | | 170 | | | | | 175 | |
| Ser | Val | Leu | Ser | Tyr | Ile | Thr | Leu | Arg | Leu | Leu | Gly | Glu | Gly | Pro | Asn |
| | | | 180 | | | | | 185 | | | | | 190 | | |
| Asp | Gly | Gln | Gly | Glu | Met | Glu | Lys | Ala | Arg | Asp | Trp | Ile | Leu | Gly | His |
| | | 195 | | | | | 200 | | | | | 205 | | | |
| Gly | Gly | Ala | Thr | Tyr | Ile | Thr | Ser | Trp | Gly | Lys | Met | Trp | Leu | Ser | Val |
| | 210 | | | | | 215 | | | | | 220 | | | | |
| Leu | Gly | Val | Tyr | Glu | Trp | Ser | Gly | Asn | Asn | Pro | Leu | Pro | Pro | Glu | Ile |
| 225 | | | | | 230 | | | | | 235 | | | | | 240 |
| Trp | Leu | Leu | Pro | Tyr | Met | Leu | Pro | Phe | His | Pro | Gly | Arg | Met | Trp | Cys |
| | | | | 245 | | | | | 250 | | | | | 255 | |
| His | Cys | Arg | Met | Val | Tyr | Leu | Pro | Met | Ser | Tyr | Leu | Tyr | Gly | Lys | Arg |
| | | | 260 | | | | | 265 | | | | | 270 | | |
| Phe | Val | Gly | Pro | Ile | Ser | Pro | Thr | Val | Leu | Ser | Leu | Arg | Lys | Glu | Leu |
| | | 275 | | | | | 280 | | | | | 285 | | | |
| Tyr | Thr | Val | Pro | Tyr | His | Asp | Ile | Asp | Trp | Asp | Gln | Ala | Arg | Asn | Leu |
| | 290 | | | | | 295 | | | | | 300 | | | | |
| Cys | Ala | Lys | Glu | Asp | Leu | Tyr | Tyr | Pro | His | Pro | Leu | Val | Gln | Asp | Ile |
| 305 | | | | | 310 | | | | | 315 | | | | | 320 |
| Leu | Trp | Ala | Ser | Leu | His | Lys | Phe | Leu | Glu | Pro | Ile | Leu | Met | His | Trp |
| | | | | 325 | | | | | 330 | | | | | 335 | |
| Pro | Gly | Lys | Arg | Leu | Arg | Glu | Lys | Ala | Ile | Ile | Ser | Ala | Leu | Glu | His |
| | | | 340 | | | | | 345 | | | | | 350 | | |
| Ile | His | Tyr | Glu | Asp | Glu | Asn | Thr | Arg | Tyr | Ile | Cys | Ile | Gly | Pro | Val |
| | | 355 | | | | | 360 | | | | | 365 | | | |
| Asn | Lys | Val | Leu | Asn | Met | Leu | Cys | Cys | Trp | Val | Glu | Asp | Pro | Asn | Ser |
| | 370 | | | | | 375 | | | | | 380 | | | | |

```
Glu Ala Phe Lys Leu His Leu Pro Arg Ile Tyr Asp Tyr Leu Trp Ile
385                 390                 395                 400

Ala Glu Asp Gly Met Lys Met Gln Gly Tyr Asn Gly Ser Gln Leu Trp
            405                 410                 415

Asp Thr Ala Phe Ala Val Gln Ala Ile Ile Ala Ser Asn Leu Ile Glu
                420                 425                 430

Glu Phe Gly Pro Thr Ile Arg Lys Ala His Thr Tyr Ile Lys Asn Ser
            435                 440                 445

Gln Val Leu Glu Asp Cys Pro Gly Asp Leu Asn Lys Trp Tyr Arg His
    450                 455                 460

Ile Ser Lys Gly Ala Trp Pro Phe Ser Thr Gly Asp His Gly Trp Pro
465                 470                 475                 480

Ile Ser Asp Cys Thr Ala Glu Gly Leu Lys Ala Val Leu Leu Leu Ser
                485                 490                 495

Lys Ile Ala Pro Glu Ile Val Gly Glu Pro Ile Asp Val Lys Arg Leu
            500                 505                 510

Tyr Asp Ser Val Asn Val Ile Leu Ser Leu Gln Asn Glu Asp Gly Gly
            515                 520                 525

Phe Ala Thr Tyr Glu Leu Lys Arg Ser Tyr Asn Trp Leu Glu Ile Ile
    530                 535                 540

Asn Pro Ala Glu Thr Phe Gly Asp Ile Val Ile Asp Tyr Pro Tyr Val
545                 550                 555                 560

Glu Cys Thr Ser Ala Ala Ile Gln Ala Leu Ala Ser Phe Arg Lys Leu
                565                 570                 575

Tyr Pro Gly His Arg Arg Glu Glu Ile Gln His Cys Ile Asp Lys Ala
            580                 585                 590

Thr Thr Phe Ile Glu Lys Ile Gln Ala Ser Asp Gly Ser Trp Tyr Gly
            595                 600                 605

Ser Trp Gly Val Cys Phe Thr Tyr Gly Ala Trp Phe Gly Val Lys Gly
            610                 615                 620

Leu Ile Ala Ala Gly Arg Ser Phe Ser Asn Cys Ser Ser Ile Arg Lys
625                 630                 635                 640

Ala Cys Glu Phe Leu Leu Ser Lys Gln Leu Pro Ser Gly Gly Trp Gly
                645                 650                 655

Glu Ser Tyr Leu Ser Cys Gln Asn Lys Val Tyr Ser Asn Leu Glu Gly
            660                 665                 670

Asn Arg Ser His Val Val Asn Thr Gly Trp Ala Met Leu Ala Leu Ile
            675                 680                 685

Asp Ala Gly Gln Ala Lys Arg Asp Ser Gln Pro Leu His Arg Ala Ala
    690                 695                 700

Ala Tyr Leu Ile Asn Ser Gln Leu Glu Asp Gly Asp Phe Pro Gln Gln
705                 710                 715                 720

Glu Ile Met Gly Val Phe Asn Lys Asn Cys Met Ile Thr Tyr Ala Ala
                725                 730                 735

Tyr Arg Asn Ile Phe Pro Ile Trp Ala Leu Gly Glu Tyr Gln Ser Gln
            740                 745                 750

Val Leu Gln Ser Arg
        755

<210> SEQ ID NO 7
<211> LENGTH: 1300
<212> TYPE: DNA
<213> ORGANISM: Triticum aestivum
```

-continued

<400> SEQUENCE: 7

```
gcacgaggac acagcttttg cagttcaagc tattgcggcc actgacctca ttgaagagtt    60
tgctcccact cttaagctgg cacatgattt tattaagaac tctcaggttg ttgatgactg   120
ccctggagat ctgagttact ggtaccgtca catatctaaa ggtgcatggc ccttttctac   180
agctgatcat ggttggccta tatcagattg cactgcagaa ggactaaagg cctcattatt   240
gctatcaaag atttctccag aaattgtggg cgaatcggtg aagttaaca gactatatga   300
tgctgtcaat tgtttgatgt cttggatgaa tgaaaatggt ggcttcgcaa catatgaact   360
ccaaaggttt tatgcctggc ttgagcttat caaccctgcc gagacattcg gagatattgt   420
gattgattac ccgtatgtgg aatgtacctc agccgcaatt caggccctga catcatttaa   480
aaagctctat cctgggcacc gcaggaaaga tgtagataac tgtatcaaca agctgctag   540
ttacattgag agcatccaaa gaaagatgg ttcatggtat ggctcttggg ctgtgtgctt   600
cacctatggc acatggttcg gagtgaaggg gctactagct gcaggtagaa ccttcaagag   660
cagtcctgca atcagaaagg catgtgactt tctgatgtca aaagagcttc ctttcggtgg   720
ctggggagaa agctatctgt catctcaaga tcaggtttac accaatcttg aagggaagca   780
tactcatgct gtcaacactg gctgggccat gctgactcta attgacgcag acaggctga   840
gagagacccg acgcctctgc atcgagcagc gaaggttttg ataaacttac aatcagagga   900
tggggaattt cctcagcaag agatcatggg agtcttcaac aagaactgca tgatcagcta   960
ctcccagtat cggaacatct ccctatctg ggcgcttggc gagtaccgct gccgggtgct  1020
gggcgcggcc aagaagtagt accgtcttcc ttctcttggg ccgggttacg tgctggaaca  1080
gtgtgttct gtaataatgt tgctaggtgc aggtggagat ctggtagccg tatagatttt  1140
tttttaccat tgatgagta gaggaataaa ctggagaggg gtatatatgt cgcttgtagg  1200
gcctgtttgg ttggatacct gaacaccgtg cctggagaaa tggactgcct ggattgagcc  1260
tgagaagatt gaaaaaaaaa aaaaaaaaa aaaaaaaaa                         1300
```

<210> SEQ ID NO 8
<211> LENGTH: 345
<212> TYPE: PRT
<213> ORGANISM: Triticum aestivum

<400> SEQUENCE: 8

```
His Glu Asp Thr Ala Phe Ala Val Gln Ala Ile Ala Ala Thr Asp Leu
  1               5                  10                  15

Ile Glu Glu Phe Ala Pro Thr Leu Lys Leu Ala His Asp Phe Ile Lys
             20                  25                  30

Asn Ser Gln Val Val Asp Asp Cys Pro Gly Asp Leu Ser Tyr Trp Tyr
         35                  40                  45

Arg His Ile Ser Lys Gly Ala Trp Pro Phe Ser Thr Ala Asp His Gly
     50                  55                  60

Trp Pro Ile Ser Asp Cys Thr Ala Glu Gly Leu Lys Ala Ser Leu Leu
 65                  70                  75                  80

Leu Ser Lys Ile Ser Pro Glu Ile Val Gly Glu Ser Val Glu Val Asn
                 85                  90                  95

Arg Leu Tyr Asp Ala Val Asn Cys Leu Met Ser Trp Met Asn Glu Asn
            100                 105                 110

Gly Gly Phe Ala Thr Tyr Glu Leu Gln Arg Phe Tyr Ala Trp Leu Glu
        115                 120                 125

Leu Ile Asn Pro Ala Glu Thr Phe Gly Asp Ile Val Ile Asp Tyr Pro
```

```
                130                  135                  140
Tyr Val Glu Cys Thr Ser Ala Ala Ile Gln Ala Leu Thr Ser Phe Lys
145                  150                  155                  160

Lys Leu Tyr Pro Gly His Arg Arg Lys Asp Val Asp Asn Cys Ile Asn
                165                  170                  175

Lys Ala Ala Ser Tyr Ile Glu Ser Ile Gln Arg Lys Asp Gly Ser Trp
                180                  185                  190

Tyr Gly Ser Trp Ala Val Cys Phe Thr Tyr Gly Thr Trp Phe Gly Val
                195                  200                  205

Lys Gly Leu Leu Ala Ala Gly Arg Thr Phe Lys Ser Ser Pro Ala Ile
210                  215                  220

Arg Lys Ala Cys Asp Phe Leu Met Ser Lys Glu Leu Pro Phe Gly Gly
225                  230                  235                  240

Trp Gly Glu Ser Tyr Leu Ser Ser Gln Asp Gln Val Tyr Thr Asn Leu
                245                  250                  255

Glu Gly Lys His Thr His Ala Val Asn Thr Gly Trp Ala Met Leu Thr
                260                  265                  270

Leu Ile Asp Ala Gly Gln Ala Glu Arg Asp Pro Thr Pro Leu His Arg
                275                  280                  285

Ala Ala Lys Val Leu Ile Asn Leu Gln Ser Glu Asp Gly Glu Phe Pro
290                  295                  300

Gln Gln Glu Ile Met Gly Val Phe Asn Lys Asn Cys Met Ile Ser Tyr
305                  310                  315                  320

Ser Gln Tyr Arg Asn Ile Phe Pro Ile Trp Ala Leu Gly Glu Tyr Arg
                325                  330                  335

Cys Arg Val Leu Gly Ala Ala Lys Lys
                340                  345

<210> SEQ ID NO 9
<211> LENGTH: 1457
<212> TYPE: DNA
<213> ORGANISM: Zea mays

<400> SEQUENCE: 9
caaagatgga agaaacacaa agcttgctta tcccttagag aagttccatt ctgatgttgc      60
tggtaggagc tttcacaatg ggaggtttat acagaggatg cgtcagaaag ctgcgtcttt     120
gcccaatgtt caattagaac aaggaactgt tacatcactt ctcgaagaaa atggtactgt     180
taaggtgtt caatacaaaa ccaagtcagg tgaagaacta aaagcttatg cgcccttgac      240
gattgtatgt gatggctgct tttcaaatct acggcgtgcc ctttgctctc caaaagttga     300
tgttccatca tgttttgttg ggctggtatt ggagaattgc caacttccac atccaaacca     360
tggccatgtt atcttggcca atccttcgcc aatactattt tacccaatta gcagcacaga     420
ggtgcgctgt ttggttgatg tcccaggtca gaaggtgcct tccatagcta gcggtgaaat     480
ggcaaattat ctcaaaaccg tcgttgcacc ccagattcct ccagaaatct atgactcttt     540
catagcggcc attgataagg gaagcataag aacaatgcca acaggagca tgccagcggc      600
tccacttcct accctggcg cacttctgat gggggatgcc ttcaatatga cacccttt       660
aactggtgga ggaatgactg ttgcattatc cgacatcgtt gtcctacgta atcttctcaa     720
gcctctccgc aatctccacg acgcatcttc cctgtgcaag tacctcgaat cgttctatac     780
gctgcggaag ccggttgcct ccaccataaa cgttggcc ggtgctctgt acaaggtctt       840
cagcgcctcg cctgatcaag ctaggaacga gatgcgccag gcctgttttg attacttgag     900
```

-continued

```
cctcggaggc gtcttctcga atgggcctat tgccttactc tcgggtctta atcctcggcc    960
actgagttta gttgcacact tcttcgctgt cgctatctac ggtgttggtc gcttgatgct   1020
ccctcttcct tcgcctaaac ggatgtggat tggagccagg ctgatttctg gtgcatgcgg   1080
catcatcctc ccgatcatca aagctgaagg cgtgagacag atgttcttcc ctgccactgt   1140
gcccgcatat taccgggctg cgcctacggg agaataagta aagcgagaac cgattccggg   1200
ctgctgcagt gctgctgatc ccaccatgat ctgatggcaa ctgatgtgtc atggatggca   1260
tttttttcct gtgttagtgg ttgttaggtg gtttgttgtg ctgctgtcat ggaatgagg    1320 aacctgtata gtgtgcccct gggtactggt caaagttggg aaatatgttg ggtcctaccg   1380
tagccatgtc gattactgcc aagctgtata tgattctgtc gaactagtga aacctctccc   1440
catctttaac gcgtatc                                                  1457
```

<210> SEQ ID NO 10
<211> LENGTH: 386
<212> TYPE: PRT
<213> ORGANISM: Zea mays

<400> SEQUENCE: 10

```
Asp Gly Arg Asn Thr Lys Leu Ala Tyr Pro Leu Glu Lys Phe His Ser
 1               5                  10                  15

Asp Val Ala Gly Arg Ser Phe His Asn Gly Arg Phe Ile Gln Arg Met
            20                  25                  30

Arg Gln Lys Ala Ala Ser Leu Pro Asn Val Gln Leu Glu Gln Gly Thr
        35                  40                  45

Val Thr Ser Leu Leu Glu Glu Asn Gly Thr Val Lys Gly Val Gln Tyr
    50                  55                  60

Lys Thr Lys Ser Gly Glu Glu Leu Lys Ala Tyr Ala Pro Leu Thr Ile
65                  70                  75                  80

Val Cys Asp Gly Cys Phe Ser Asn Leu Arg Arg Ala Leu Cys Ser Pro
                85                  90                  95

Lys Val Asp Val Pro Ser Cys Phe Val Gly Leu Val Leu Glu Asn Cys
            100                 105                 110

Gln Leu Pro His Pro Asn His Gly His Val Ile Leu Ala Asn Pro Ser
        115                 120                 125

Pro Ile Leu Phe Tyr Pro Ile Ser Ser Thr Glu Val Arg Cys Leu Val
    130                 135                 140

Asp Val Pro Gly Gln Lys Val Pro Ser Ile Ala Ser Gly Glu Met Ala
145                 150                 155                 160

Asn Tyr Leu Lys Thr Val Val Ala Pro Gln Ile Pro Pro Glu Ile Tyr
                165                 170                 175

Asp Ser Phe Ala Ala Ile Asp Lys Gly Ser Ile Arg Thr Met Pro Asn
            180                 185                 190

Arg Ser Met Pro Ala Ala Pro Leu Pro Thr Pro Gly Ala Leu Leu Met
        195                 200                 205

Gly Asp Ala Phe Asn Met Arg His Pro Leu Thr Gly Gly Gly Met Thr
    210                 215                 220

Val Ala Leu Ser Asp Ile Val Val Leu Arg Asn Leu Leu Lys Pro Leu
225                 230                 235                 240

Arg Asn Leu His Asp Ala Ser Ser Leu Cys Lys Tyr Leu Glu Ser Phe
                245                 250                 255

Tyr Thr Leu Arg Lys Pro Val Ala Ser Thr Ile Asn Thr Leu Ala Gly
            260                 265                 270
```

```
Ala Leu Tyr Lys Val Phe Ser Ala Ser Pro Asp Gln Ala Arg Asn Glu
            275                 280                 285

Met Arg Gln Ala Cys Phe Asp Tyr Leu Ser Leu Gly Gly Val Phe Ser
        290                 295                 300

Asn Gly Pro Ile Ala Leu Leu Ser Gly Leu Asn Pro Arg Pro Leu Ser
305                 310                 315                 320

Leu Val Ala His Phe Phe Ala Val Ala Ile Tyr Gly Val Gly Arg Leu
                325                 330                 335

Met Leu Pro Leu Pro Ser Pro Lys Arg Met Trp Ile Gly Ala Arg Leu
        340                 345                 350

Ile Ser Gly Ala Cys Gly Ile Ile Leu Pro Ile Ile Lys Ala Glu Gly
            355                 360                 365

Val Arg Gln Met Phe Phe Pro Ala Thr Val Pro Ala Tyr Tyr Arg Ala
        370                 375                 380

Ala Pro
385

<210> SEQ ID NO 11
<211> LENGTH: 1289
<212> TYPE: DNA
<213> ORGANISM: Oryza sativa

<400> SEQUENCE: 11
aagaagatgg tacagttaag ggtgttaaat acaagaccaa gtcaggtgaa gaattaaaag       60
catatgcacc tctgacaatt gtatgcgatg gctgtttctc aaaccgcacg agcttacatt      120
gctctccaaa ggttgatgta ccatcttgtt ttgttgggct ggtcctggag aattgtcaac      180
ttcctcatgc aaaccatggc catgttgtcc tggccaatcc ttcacctatc ctatttacc       240 caataagcag cactgaagtt cgctgtttgg ttgatgtccc tggtcagaag gtgccttcca      300
tagcaaacgg tgaaatggca aaatatctca aaacagtggt tgcacctcag attcctccag      360
aaatctatga ttcattcata gcagccattg ataagggaag cataagaaca atgccaaaca      420
ggagcatgcc ggctgctcca catccaaccc ctggtgcact tttgatgggt gatgcattca      480
acatgcggca tcctttgact ggtggcggaa tgactgttgc attatctgac attgttgtgc      540
tacgtaatct tctcaagcct ctccgcaatc tgcatgatgc atctgctctt tgcaaatacc      600
ttgaatcatt ctatacactg cggaagccgg ttgcttctac cataaacaca ttagctggtg      660
ctctatacaa ggttttcagt gcctcacctg atcaggctag gaatgagatg cgccaagcct      720
gctttgatta cttgagcctt ggaggtgtct tttcaaatgg gcctactgct cttctgtctg      780
gtctgaatcc tcgaccattg agtttagtgg cacatttctt tgctgtcgct atctatggtg      840
tcggtcgcct aatgcttccc ctcccttcac ctaaacgcat gtggatcggc gtaagactga      900
tttccagtgc atgtggtata attttcccca tcatcaaagc tgaaggtgtg aggcatatgt      960
tcttccccgc cactgtccct gcctattatc gtgctcctcg tccaatggag taagggggga     1020
aaatgaaagg agaagcgaag agaaaatccc tgccactgtc ctgatcggcg gatgttttc     1080 gtggatggca attttcctgt gtaattggta gtagtcgtca ggccgtgagg ttgtgtgtgc     1140
tgttgttcta atggaacgag gggacctgta tacaccgtca cattcctgt acacttgcca      1200 ctttcgttgt tccgtcaggg atgcatgtcg actgctaatc cttaagctgt atatccccca     1260
tgaattcatc atgattgcgt ctttgctct                                       1289

<210> SEQ ID NO 12
<211> LENGTH: 330
```

<212> TYPE: PRT
<213> ORGANISM: Oryza sativa

<400> SEQUENCE: 12

```
Gly Thr Val Lys Gly Val Lys Tyr Lys Thr Lys Ser Gly Glu Glu Leu
 1               5                  10                  15

Lys Ala Tyr Ala Pro Leu Thr Ile Val Cys Asp Gly Cys Phe Ser Asn
             20                  25                  30

Arg Thr Ser Leu His Cys Ser Pro Lys Val Asp Val Pro Ser Cys Phe
         35                  40                  45

Val Gly Leu Val Leu Glu Asn Cys Gln Leu Pro His Ala Asn His Gly
     50                  55                  60

His Val Val Leu Ala Asn Pro Ser Pro Ile Leu Phe Tyr Pro Ile Ser
 65                  70                  75                  80

Ser Thr Glu Val Arg Cys Leu Val Asp Val Pro Gly Gln Lys Val Pro
                 85                  90                  95

Ser Ile Ala Asn Gly Glu Met Ala Lys Tyr Leu Lys Thr Val Val Ala
            100                 105                 110

Pro Gln Ile Pro Pro Glu Ile Tyr Asp Ser Phe Ile Ala Ala Ile Asp
        115                 120                 125

Lys Gly Ser Ile Arg Thr Met Pro Asn Arg Ser Met Pro Ala Ala Pro
    130                 135                 140

His Pro Thr Pro Gly Ala Leu Leu Met Gly Asp Ala Phe Asn Met Arg
145                 150                 155                 160

His Pro Leu Thr Gly Gly Gly Met Thr Val Ala Leu Ser Asp Ile Val
                165                 170                 175

Val Leu Arg Asn Leu Leu Lys Pro Leu Arg Asn Leu His Asp Ala Ser
            180                 185                 190

Ala Leu Cys Lys Tyr Leu Glu Ser Phe Tyr Thr Leu Arg Lys Pro Val
        195                 200                 205

Ala Ser Thr Ile Asn Thr Leu Ala Gly Ala Leu Tyr Lys Val Phe Ser
    210                 215                 220

Ala Ser Pro Asp Gln Ala Arg Asn Glu Met Arg Gln Ala Cys Phe Asp
225                 230                 235                 240

Tyr Leu Ser Leu Gly Gly Val Phe Ser Asn Gly Pro Thr Ala Leu Leu
                245                 250                 255

Ser Gly Leu Asn Pro Arg Pro Leu Ser Leu Val Ala His Phe Phe Ala
            260                 265                 270

Val Ala Ile Tyr Gly Val Gly Arg Leu Met Leu Pro Leu Pro Ser Pro
        275                 280                 285

Lys Arg Met Trp Ile Gly Val Arg Leu Ile Ser Ser Ala Cys Gly Ile
    290                 295                 300

Ile Phe Pro Ile Ile Lys Ala Glu Gly Val Arg His Met Phe Phe Pro
305                 310                 315                 320

Ala Thr Val Pro Ala Tyr Tyr Arg Ala Pro
                325                 330
```

<210> SEQ ID NO 13
<211> LENGTH: 1883
<212> TYPE: DNA
<213> ORGANISM: Glycine max

<400> SEQUENCE: 13

```
gcacgaggaa actagagcca gaaagagaaa caaagagagc gagagcgaga gcgaaaacac    60
ctcaacgtcg tcgtcgtagc cgagaggttc ctcgcaatgg tggacccta cgtgctcgga   120
```

-continued

```
tggatcatat gcgccgtgct cagcctcgtc gcgcttcgca atttcgcttt cgcgcggaag    180
aaccgttgcc attcgtctga gaccgatgcc actcgccgcg cggaaaatgt caccaccgcc    240
gccggagaat gcagatcctc gagtcgcgac ggcgacgttg acgtcattat tgtcggagct    300
ggtgtcgccg gctccgctct cgctcacact ctcggcaagg atgggcgtcg ggtacttgtc    360
attgaaagag atttgagtga acaagaccga attgttgggg agttgctaca acctggaggc    420
tatctcaaat taattgagct gggacttgaa gattgtgtgg agaaaattga tgctcaacta    480
gtgtttggtt atgctctttt caaggatggg aagcacacaa gactctctta tcccttggaa    540
aagtttcact cagatgttgc tggcagaagc tttcacaatg gcgttttat tcagaggatg     600 agagagaagg ctgcctccct ttccaatgta cgactggagc aaggaacagt cacttccta    660 cttgaagaga agggggttat taaggtgtg cactacaaaa cgaaggatag tcaagaatta    720
tcagcttgtg cacccttac cgttgtttgt gatggctgtt tctcaaactt gcgccgatct    780
ctttgtaatc ctaaggtaga tgttccctct catttcgttg gcttaatttt ggagagttgt    840
gaacttcctt atgctaatca tggccatgtc atactgggga tccttcgcc agttctgttc     900 tatcggataa gtagttcaga aattcgttgt ctggttgatg ttcctggtca gaaggttcca    960
tctatttcga atggtgaaat gacaaattat ttgaagacag tggtagctcc acagattcca   1020
cctgagcttc atgactcatt cgtagctgca gtggacaaag gcaacatcag gacaatgcca   1080
aacagaagca tgccagcagc tccttatcct acgcccggag ccctgttgat gggagatgca   1140
ttcaacatgc gccatcctct aaccgggggt ggaatgactg tggcattatc tgacatagta   1200
gtgctgcgaa atcttctgag acctttgcgt gacctgaatg atgcacctgg cctttgcaaa   1260
tacctagaat cctttttatac cttacgcaag cctgtggcat ccactataaa tacgttggca   1320
ggagcacttt acaaggtttt tgcgcatca cctgatccag caaggaagga atgcgccaa    1380 gcttgcttcg attatcttag tcttggaggt ctattctcgg aagggccagt ctctttgctt   1440
tcaggattaa accctcggcc cttgagcctg ttctccatt tctttgctgt tgcaatatat    1500
ggtgttggcc gtttactgct accattcct tcacctaaac ggatgtggat tggagtccga   1560
ttaatttcta gtgcatctgg aatcatcttg ccaataatta aggcagaagg agtccgtcag   1620
atgttcttcc ctgcaactgt tccagcttac tatagaaatc ccccggccca ataaatgtga   1680
gttccgtgaa cccatcatga gtcattcaag atgagccacc agtgtttcc attcagaaaa    1740 ttaacgggtt caattgagat gtttgcaaac aatctggctt tagtgtcatg taaagtcgat   1800
tttaaattaa atgtttgatt tgttaatctt cttaaaaaa aaaaaaaaa aaaaaaaaa     1860 aaaaaaaaaa aaaaaaaaaa aaa                                           1883
```

<210> SEQ ID NO 14
<211> LENGTH: 523
<212> TYPE: PRT
<213> ORGANISM: Glycine max

<400> SEQUENCE: 14

```
Met Val Asp Pro Tyr Val Leu Gly Trp Ile Ile Cys Ala Val Leu Ser
  1               5                  10                  15

Leu Val Ala Leu Arg Asn Phe Ala Phe Ala Arg Lys Asn Arg Cys His
             20                  25                  30

Ser Ser Glu Thr Asp Ala Thr Arg Ala Glu Asn Val Thr Thr Ala
         35                  40                  45

Ala Gly Glu Cys Arg Ser Ser Ser Arg Asp Gly Asp Val Asp Val Ile
```

-continued

```
            50                  55                  60
Ile Val Gly Ala Gly Val Ala Gly Ser Ala Leu Ala His Thr Leu Gly
 65                  70                  75                  80
Lys Asp Gly Arg Arg Val Leu Val Ile Glu Arg Asp Leu Ser Glu Gln
                     85                  90                  95
Asp Arg Ile Val Gly Glu Leu Leu Gln Pro Gly Gly Tyr Leu Lys Leu
                100                 105                 110
Ile Glu Leu Gly Leu Glu Asp Cys Val Glu Lys Ile Asp Ala Gln Leu
                115                 120                 125
Val Phe Gly Tyr Ala Leu Phe Lys Asp Gly Lys His Thr Arg Leu Ser
                130                 135                 140
Tyr Pro Leu Glu Lys Phe His Ser Asp Val Ala Gly Arg Ser Phe His
145                 150                 155                 160
Asn Gly Arg Phe Ile Gln Arg Met Arg Glu Lys Ala Ala Ser Leu Ser
                    165                 170                 175
Asn Val Arg Leu Glu Gln Gly Thr Val Thr Ser Leu Leu Glu Glu Lys
                180                 185                 190
Gly Val Ile Lys Gly Val His Tyr Lys Thr Lys Asp Ser Gln Glu Leu
                195                 200                 205
Ser Ala Cys Ala Pro Leu Thr Val Val Cys Asp Gly Cys Phe Ser Asn
                210                 215                 220
Leu Arg Arg Ser Leu Cys Asn Pro Lys Val Asp Val Pro Ser His Phe
225                 230                 235                 240
Val Gly Leu Ile Leu Glu Ser Cys Glu Leu Pro Tyr Ala Asn His Gly
                    245                 250                 255
His Val Ile Leu Gly Asp Pro Ser Pro Val Leu Phe Tyr Arg Ile Ser
                260                 265                 270
Ser Ser Glu Ile Arg Cys Leu Val Asp Val Pro Gly Gln Lys Val Pro
                275                 280                 285
Ser Ile Ser Asn Gly Glu Met Thr Asn Tyr Leu Lys Thr Val Val Ala
                290                 295                 300
Pro Gln Ile Pro Pro Glu Leu His Asp Ser Phe Val Ala Ala Val Asp
305                 310                 315                 320
Lys Gly Asn Ile Arg Thr Met Pro Asn Arg Ser Met Pro Ala Ala Pro
                    325                 330                 335
Tyr Pro Thr Pro Gly Ala Leu Leu Met Gly Asp Ala Phe Asn Met Arg
                340                 345                 350
His Pro Leu Thr Gly Gly Gly Met Thr Val Ala Leu Ser Asp Ile Val
                355                 360                 365
Val Leu Arg Asn Leu Leu Arg Pro Leu Arg Asp Leu Asn Asp Ala Pro
                370                 375                 380
Gly Leu Cys Lys Tyr Leu Glu Ser Phe Tyr Thr Leu Arg Lys Pro Val
385                 390                 395                 400
Ala Ser Thr Ile Asn Thr Leu Ala Gly Ala Leu Tyr Lys Val Phe Cys
                    405                 410                 415
Ala Ser Pro Asp Pro Ala Arg Lys Glu Met Arg Gln Ala Cys Phe Asp
                420                 425                 430
Tyr Leu Ser Leu Gly Gly Leu Phe Ser Glu Gly Pro Val Ser Leu Leu
                435                 440                 445
Ser Gly Leu Asn Pro Arg Pro Leu Ser Leu Val Leu His Phe Phe Ala
                450                 455                 460
Val Ala Ile Tyr Gly Val Gly Arg Leu Leu Leu Pro Phe Pro Ser Pro
465                 470                 475                 480
```

```
Lys Arg Met Trp Ile Gly Val Arg Leu Ile Ser Ala Ser Gly Ile
                485                 490                 495

Ile Leu Pro Ile Ile Lys Ala Glu Gly Val Arg Gln Met Phe Phe Pro
            500                 505                 510

Ala Thr Val Pro Ala Tyr Tyr Arg Asn Pro Pro
            515                 520

<210> SEQ ID NO 15
<211> LENGTH: 1948
<212> TYPE: DNA
<213> ORGANISM: Triticum aestivum

<400> SEQUENCE: 15
```

| | | | | | |
|---|---|---|---|---|---|
| gcacgagctc | tcgtctcgtc | tcgtctctcg | tcccaatccc | atcgcccggc | actctccccc | 60 |
| gctcgtctcc | tccccgcacg | catcaccctc | tctcccctcg | cccggtcgaa | gggatccccg | 120 |
| cgccggagga | cggctgcgcg | gtcgctgacg | gcgcagggag | cgcggccgtg | gacggcccga | 180 |
| cggacgtcat | catcgtcgga | gccggggtcg | ccggatctgc | cctcgcctac | acgctcggaa | 240 |
| aggatggtcg | acgggtgcat | gtcatagaga | gagacctgac | agagcctgat | agaattgtgg | 300 |
| gtgaattgtt | acaacctgga | ggctacctga | aattgatgga | attgggtctg | caggactgcg | 360 |
| ttgatgaaat | tgatgcacag | cgtgtccttg | gttatgcatt | attcaaagat | gggaagaaca | 420 |
| caaaactttc | ttaccccttg | gagaagttcc | attcagatgt | ggctggcagg | agctttcaca | 480 |
| atggacggtt | catacagagg | atgcgagaaa | aggctgcatc | tttgcccaat | gtccaactgg | 540 |
| agcaaggaac | agttacatct | ttgcttgaag | aaaatggtac | agttaagggt | gtgcaataca | 600 |
| agatcaagtc | aggtgaagaa | ctaaaagctt | atgcaccatt | gacaattgta | tgtgatggct | 660 |
| gcttttcaaa | cttaagacgt | gcccttttgct | ctccaaaggt | tgaggtgccg | tcttgctttg | 720 |
| ttggcctggt | cttggagaat | tgtgaacttc | tcatgcgaa | ccatggccat | gttatcttgg | 780 |
| ccaatccttc | tcccatccta | ttttacccga | taagcagcac | cgaggttcgc | tgtttggtag | 840 |
| atgtccctgg | tcagaaggtg | ccttccatag | caagtggtga | aatgacaaat | tatctcaaga | 900 |
| ccgtggttgc | acctcagatt | cctccacaaa | tctgtgattc | ttttatagca | gcaattgata | 960 |
| agggaagcat | aagaacaatg | ccaaatagga | gcatgccagc | tgcaccacat | ccaacacctg | 1020 |
| gtgcactttt | gatgggagat | gctttcaata | tgcgacaccc | tttaacaggt | ggaggaatga | 1080 |
| ctgttgcatt | atcagatata | gtcgtcctgc | gtaatcttat | caagcttctt | cgcaatctgc | 1140 |
| atgatgcctc | tgccctctgc | aaatacctcg | agtcattcta | tactctgcgg | aagccggttg | 1200 |
| cttctacaat | aaaacacattg | gctggtgctc | tatacaaagt | cttcagttcc | tcgcctgaca | 1260 |
| aggctaggga | tgagatgcgc | caagcttgct | tgattactt | gagccttgga | ggtgtctgtt | 1320 |
| caaatgggcc | cattgctcta | ctctccggtc | ttaatcctcg | gccattgagt | ttggttgcac | 1380 |
| acttctttgc | tgttgctatc | tttggtgttg | gacgactgat | gctcccccctt | ccttcaccta | 1440 |
| aacgaatgtg | gactggagcg | agattgattt | caggtgcatg | tggtatcatc | ttcccaatca | 1500 |
| tcaaagctga | aggtgtgagg | caaatgttct | tccctgctac | cgtccccgcg | tattaccggg | 1560 |
| ctcctcccga | agcggagttc | tgaatgacga | aggtgcagct | aatctctctt | gcacgatgac | 1620 |
| atttttccct | gtgtcggtag | tcgtctacag | tgttagccgg | tcactggaat | gtgctgtgtt | 1680 |
| ggtagtctga | atggatcgag | gaacgtgtat | agtatctccg | ctgggtgctg | atcctgtttt | 1740 |
| tgaaatgttt | tgaattgctg | cgtcggtgcc | catgttgatt | cgtcctagtg | aaattgtaca | 1800 |
| tctttgttgt | actacgcccct | ccgttccgaa | ttacttgtcg | cacttatgga | tgtatcaaga | 1860 |

-continued

```
tgtattttag ttctagatac atccatttta acgacgagta atttggaaaa aaaaaaaaaa       1920
aaaaaaaaaa aaaaaaaaaa aaaaaaaa                                          1948
```

<210> SEQ ID NO 16
<211> LENGTH: 467
<212> TYPE: PRT
<213> ORGANISM: Triticum aestivum

<400> SEQUENCE: 16

```
Val Asp Gly Pro Thr Asp Val Ile Ile Val Gly Ala Gly Val Ala Gly
 1               5                  10                  15

Ser Ala Leu Ala Tyr Thr Leu Gly Lys Asp Gly Arg Arg Val His Val
             20                  25                  30

Ile Glu Arg Asp Leu Thr Glu Pro Asp Arg Ile Val Gly Glu Leu Leu
         35                  40                  45

Gln Pro Gly Gly Tyr Leu Lys Leu Met Glu Leu Gly Leu Gln Asp Cys
     50                  55                  60

Val Asp Glu Ile Asp Ala Gln Arg Val Leu Gly Tyr Ala Leu Phe Lys
 65                  70                  75                  80

Asp Gly Lys Asn Thr Lys Leu Ser Tyr Pro Leu Glu Lys Phe His Ser
                 85                  90                  95

Asp Val Ala Gly Arg Ser Phe His Asn Gly Arg Phe Ile Gln Arg Met
            100                 105                 110

Arg Glu Lys Ala Ala Ser Leu Pro Asn Val Gln Leu Glu Gln Gly Thr
        115                 120                 125

Val Thr Ser Leu Leu Glu Glu Asn Gly Thr Val Lys Gly Val Gln Tyr
    130                 135                 140

Lys Ile Lys Ser Gly Glu Glu Leu Lys Ala Tyr Ala Pro Leu Thr Ile
145                 150                 155                 160

Val Cys Asp Gly Cys Phe Ser Asn Leu Arg Arg Ala Leu Cys Ser Pro
                165                 170                 175

Lys Val Glu Val Pro Ser Cys Phe Val Gly Leu Val Leu Glu Asn Cys
            180                 185                 190

Glu Leu Pro His Ala Asn His Gly His Val Ile Leu Ala Asn Pro Ser
        195                 200                 205

Pro Ile Leu Phe Tyr Pro Ile Ser Ser Thr Glu Val Arg Cys Leu Val
    210                 215                 220

Asp Val Pro Gly Gln Lys Val Pro Ser Ile Ala Ser Gly Glu Met Thr
225                 230                 235                 240

Asn Tyr Leu Lys Thr Val Val Ala Pro Gln Ile Pro Pro Gln Ile Cys
                245                 250                 255

Asp Ser Phe Ile Ala Ala Ile Asp Lys Gly Ser Ile Arg Thr Met Pro
            260                 265                 270

Asn Arg Ser Met Pro Ala Ala Pro His Pro Thr Pro Gly Ala Leu Leu
        275                 280                 285

Met Gly Asp Ala Phe Asn Met Arg His Pro Leu Thr Gly Gly Gly Met
    290                 295                 300

Thr Val Ala Leu Ser Asp Ile Val Val Leu Arg Asn Leu Ile Lys Leu
305                 310                 315                 320

Leu Arg Asn Leu His Asp Ala Ser Ala Leu Cys Lys Tyr Leu Glu Ser
                325                 330                 335

Phe Tyr Thr Leu Arg Lys Pro Val Ala Ser Thr Ile Asn Thr Leu Ala
            340                 345                 350
```

-continued

```
Gly Ala Leu Tyr Lys Val Phe Ser Ser Ser Pro Asp Lys Ala Arg Asp
        355                 360             365

Glu Met Arg Gln Ala Cys Phe Asp Tyr Leu Ser Leu Gly Gly Val Cys
    370             375             380

Ser Asn Gly Pro Ile Ala Leu Leu Ser Gly Leu Asn Pro Arg Pro Leu
385             390             395             400

Ser Leu Val Ala His Phe Phe Ala Val Ala Ile Phe Gly Val Gly Arg
            405             410             415

Leu Met Leu Pro Leu Pro Ser Pro Lys Arg Met Trp Thr Gly Ala Arg
            420             425             430

Leu Ile Ser Gly Ala Cys Gly Ile Ile Phe Pro Ile Ile Lys Ala Glu
        435             440             445

Gly Val Arg Gln Met Phe Phe Pro Ala Thr Val Pro Ala Tyr Tyr Arg
    450             455             460

Ala Pro Pro
465
```

ENZYMES INVOLVED IN SQUALENE METABOLISM

This application claims priority benefit of U.S. Provisional Application No. 60/105,405 filed Oct. 23, 1998, now pending.

FIELD OF THE INVENTION

This invention is in the field of plant molecular biology. More specifically, this invention pertains to nucleic acid fragments encoding enzymes involved in squalene metabolism in plants and seeds.

BACKGROUND OF THE INVENTION

The terpenoids constitute the largest family of natural products with over 22,000 individual compounds of this class having been described. The terpenoids play diverse functional roles in plants as hormones, photosynthetic pigments, electron carriers, mediators of polysccharide assembly, and structural components of membranes. Farnesyl pyrophosphate is converted to squalene in the first dedicated step towards sterol biosynthesis. Squalene is then converted to squalene-2,3-epoxide which, in photosynthetic organisms, is converted cycloarterenol.

Squalene monooxidase (EC 1.14.99.7), also referred to as squalene epoxidase, is an oxidoreductase which acts on paired donors with incorporation of molecular oxygen. This enzyme is located at the endoplasmic reticulum, and catalyzes the conversion of squalene to squalene 2,3-epoxide in the pathway to produce sterol. Squalene monooxygenase may be the rate limiting step in sterol biosynthesis. Oxygen, NADPH, FAD, and a cytosolic protein are required for squalene monooxygenase function. Squalene monooxygenase together with lanosterol synthase was formerly known as squalene oxydocyclase.

Whereas vertebrates and fungi synthesize sterols from epoxysqualene through the intermediate lanosterol, plants cyclize epoxysqualene to cycloartenol as the initial sterol. This reaction is catalyzed by cycloartenol synthase (EC 5.4.99.8), also called 2,3-epoxysqualene-cycloartenol cyclase.

Sequences encoding peptides with similarities to cycloartenol synthase and squalene monooxygenase are found in the NCBI database having General Identifier Nos. 5566676, 5468642, 5706248, 5608422, 5055959, 2309779, 2310417, 3107671, 702331, and 4874404.

SUMMARY OF THE INVENTION

The present invention relates to isolated polynucleotides comprising a nucleotide sequence encoding a first polypeptide of at least 200 amino acids that has at least 90% identity based on the Clustal method of alignment when compared to a polypeptide selected from the group consisting of a corn cycloartenol synthase polypeptide of SEQ ID NO:2, a rice cycloartenol synthase polypeptide of SEQ ID NO:4, a soybean cycloartenol synthase polypeptide of SEQ ID NO:6, and a wheat cycloartenol synthase polypeptide of SEQ ID NO:8. The present invention also relates to isolated polynucleotides comprising a nucleotide sequence encoding a first polypeptide of at least 200 amino acids that has at least 90% identity based on the Clustal method of alignment when compared to a polypeptide selected from the group consisting of a corn squalene monooxygenase polypeptide of SEQ ID NO:10, a rice squalene monooxygenase polypeptide of SEQ ID NO:12, a soybean squalene monooxygenase polypeptide of SEQ ID NO:14, and a wheat squalene monooxygenase polypeptide of SEQ ID NO:16. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, and 15 that codes for a polypeptide selected from the group consisting of SEQ ID NOs:2, 4, 6, 8, 10, 12, 14, and 16. The present invention also relates to an isolated polynucleotide comprising a nucleotide sequences of at least 40 (preferably at least 30 or at least 15) contiguous nucleotides derived from a nucleotide sequence selected from the group consisting of SEQ ID NOs:1, 3, 5, 7, 9, 11, 13, 15, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell or virus. If the host cell is a virus, it is preferably a baculovirus. A virus host cell comprising an isolated polynucleotide of the present invention or a chimeric gene of the present invention is most preferred.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a cycloartenol synthase polypeptide of at least 200 amino acids comprising at least 90% homology based on the Clustal method of alignment compared to a polypeptide selected from the group consisting of SEQ ID NOs:1, 4, 6, and 8. The present invention relates to a squalene monooxygenase polypeptide of at least 200 amino acids comprising at least 90% homology based on the Clustal method of alignment compared to a polypeptide selected from the group consisting of SEQ ID NOs:10, 12, 14, and 16.

The present invention relates to a method of selecting an isolated polynucleotide that affects the level of expression of a cycloartenol synthase or a squalene monooxygenase polypeptide in a plant cell, the method comprising the steps of:

constructing an isolated polynucleotide of the present invention or an isolated chimeric gene of the present invention;

introducing the isolated polynucleotide or the isolated chimeric gene into a plant cell;

measuring the level a cycloartenol synthase or a squalene monooxygenase polypeptide in the plant cell containing the isolated polynucleotide; and comparing the level of a cycloartenol synthase or a squalene monooxygenase polypeptide in the plant cell containing the isolated polynucleotide with the level of a cycloartenol synthase or a squalene monooxygenase polypeptide in a plant cell that does not contain the isolated polynucleotide.

The present invention relates to a method of obtaining a nucleic acid fragment encoding a substantial portion of a cycloartenol synthase or a squalene monooxygenase polypeptide gene, preferably a plant cycloartenol synthase or a squalene monooxygenase polypeptide, comprising the steps of: synthesizing an oligonucleotide primer comprising a nucleotide sequence of at least 40 (preferably at least 30 or at least 15) contiguous nucleotides derived from a nucleotide sequence selected from the group consisting of SEQ ID NOs:1, 3, 5, 7, 9, 11, 13, 15, and the complement of such nucleotide sequences; and amplifying a nucleic acid fragment (preferably a cDNA inserted in a cloning vector) using the oligonucleotide primer. The amplified nucleic acid fragment preferably will encode a portion of a cycloartenol synthase or a squalene monooxygenase amino acid sequence.

The present invention also relates to a method of obtaining a nucleic acid fragment encoding all or a substantial portion of the amino acid sequence encoding a cycloartenol synthase or a squalene monooxygenase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a cycloartenol synthase or a squalene monooxygenase, the method comprising the steps of: (a) transforming a host cell with a nucleic acid fragment encoding; a cycloartenol synthase or a squalene monooxygenase polypeptide preferably operably linked to suitable regulatory sequences; (b) growing the transformed host cell under conditions that are suitable for expression of the nucleic acid fragment compound (such as the production of mRNA and/or polypeptide) wherein expression of the nucleic acid fragment preferably results in production of cycloartenol synthase or squalene monooxygenase in the transformed host cell; (c) optionally purifying the cycloartenol synthase or the squalene monooxygenase expressed by the transformed host cell; (d) treating the cycloartenol synthase or the squalene monooxygenase with a compound to be tested; and (e) comparing the activity of the cycloartenol synthase or the squalene monooxygenase that has been treated with a test compound to the activity of an untreated cycloartenol synthase or squalene monooxygenase, thereby selecting compounds with potential for inhibitory activity.

BRIEF DESCRIPTION OF THE SEQUENCE LISTING

The invention can be more fully understood from the following detailed description and the accompanying Sequences Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Enzymes Involved in Squalene Metabolism

| | | SEQ ID NO: | |
|---|---|---|---|
| Protein | Clone Designation | (Nucleotide) | (Amino Acid) |
| Corn cycloartenol synthase | cep7.pk0019.f10 | 1 | 2 |
| Rice cycloartenol synthase | r1r2.pk0004.f6 | 3 | 4 |
| Soybean cycloartenol synthase | sdp2c.pk008.g6 | 5 | 6 |
| Wheat cycloartenol synthase | wr1.pk164.h10 | 7 | 8 |
| Corn squalene monooxygenase | Contig of: | 9 | 10 |
| | csi1n.pk0037.a8 | | |
| | p0045.ckdac10r | | |
| | p0083.cldb104r | | |
| Rice squalene monooxygenase | Contig of: | 11 | 12 |
| | res1c.pk006.o13 | | |
| | r10n.pk0031.d7 | | |
| Soybean squalene monooxygenase | sdp3c.pk003.a5 | 13 | 14 |
| Wheat squalene monooxygenase | w1m1.pk0005.d6 | 15 | 16 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED: DESCRIPTION OF THE INVENTION

In the context of this disclosure, a number of terms shall be utilized. As used herein, a "polynucleotide" is a nucleotide sequence such as a nucleic acid fragment. A polynucleotide any may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least 40 contiguous nucleotides, preferably at least 30 contiguous nucleotides, most preferably at least 15 contiguous nucleotides, of the nucleic acid sequence of the SEQ ID NOs:1, 3, 5, 7, 9, 11, 13, or 15.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 40 (preferably at least 30, most preferably at least 15) contiguous nucleotides derived from a nucleotide sequence selected from the group consisting of SEQ ID NOs:1, 3, 5, 7, 9, 11, 13, 15, and the complement of such nucleotide sequences may be used in methods of selecting an isolated polynucleotide that affects the expression of a polypeptide (such as cycloartenol synthase or squalene monooxygenase) in a host cell. A method of selecting an isolated polynucleotide that affects the level of expression of a polypeptide in a host cell (eukaryotic, such as plant, or prokarotic such as yeast bacterial or virus) may comprise the steps of: constructing an isolated polynucleotide of the present invention or an isolated chimeric gene of the present invention; introducing the isolated polynucleotide or the isolated chimeric gene into a host cell; measuring the level the polypeptide in the host cell containing the isolated polynucleotide; and comparing the level of the polypeptide in the host cell containing the isolated polynucleotide with the level of the polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are 85% identical to the amino acid sequences reported herein. Preferably 90% identical to the amino acid sequences reported herein. Most preferred are nucleic acid fragments that encode amino acid sequences that are 95% identical to the amino acid sequences reported herein. Suitable nucleic acid fragments not only have the above identities but typically encode a polypeptide having at least 50 amino acids, preferably 100 amino acids, more preferably 150 amino acids, still more preferably 200 amino acids, and most preferably 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used: as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to j as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene an,d the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA, precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA,) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several enzymes involved in squalene metabolism have bee h isolated and identified by comparison of random plant CDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to,: methods of nucleic acid hybridization, and methods of DNA and RNA amplification as exemplified by various uses of nucleic acid amplification technologies (e.g., polymerase chain reaction, ligase chain reaction).

For example, genes encoding other cycloartenol synthases or squalene monooxygenases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 40 (preferably at least 30, most preferably at least 15) contiguous nucleotides derived from a nucleotide sequence selected from the group consisting of SEQ ID NOs:1, 3, 5, 7, 9, 11, 13, 15, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as cycloartenol synthase or squalene monooxygenase) preferably a substantial portion of a plant polypeptide, comprising the steps of: synthesizing an oligonucleotide primer comprising a nucleotide sequence of at least 40 (preferably at least 30, most preferably at least 15) contiguous nucleotides derived from a nucleotide sequence selected from the group consisting of SEQ ID NOs:1, 3, 5, 7, 9, 11, 13, 15, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen CDNA expression libraries to isolate full-length cDNA clones of interest (Lerner (1984) *Adv. Immunol.* 336:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the relative sterol composition in those cells. These changes in the plant seed may be useful to improve the seed nutritional value, and in the plant leaf may aid in insect tolerance. Squalene monooxygenase catalyzes one of the rate limiting steps in squalene biosynthesis and, thus, is a good herbicide target. Catalyzing an early step in sterol synthesis, squalene synthase catalyzes a required step in the synthesis of saponins in soybean seeds. Elimination of saponins might lead to improved flavor.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53,), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded enzyme involved in squalene metabolism. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in squalene biosynthesis. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses, using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153, Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (19911) Science 252:1651–1656). The resulting ESTs are analyzed using a Perkin Elmer Model 377 fluorescent sequencer.

Example 2

Identification of cDNA Clones cDNA clones encoding enzymes involved in squalene metabolism were identified by conducting BLAST (Basic Local Alignment Search Tool; Altschul et al. (1993) J. Mol. Biol. 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the

TABLE 2 cDNA Libraries from Corn, Rice, Soybean, and Wheat

| Library | Tissue | Clone |
|---------|--------|-------|
| cep7 | Corn 7 Day Old Epicotyl; Grown in Light | cep7.pk0019.f10 |
| csi1n | Corn Silk* | csi1n.pk0037.a8 |
| p0045 | Hi-II Suspension Culture | p0045.ckdac10r |
| p0083 | Corn Whole Kernels 7 Days After Pollination | p0083.cldb104r |
| res1c | Rice Etiolated Seedling | res1c.pk006.o13 |
| r10n | Rice 15 Day Old Leaf* | r10n.pk0031.d7 |
| r1r2 | Rice Leaf 15 Days After Germination, 2 Hours After Infection of Strain *Magaporthe grisea* 4360-R-62 (AVR2-YAMO); Resistant | r1r2.pk0004.f6 |
| sdp2c | Soybean Developing Pods (6–7 mm) | sdp2c.pk008.g6 |
| sdp3c | Soybean Developing Pods (8–9 mm) | sdp3c.pk003.a5 |
| w1m1 | Wheat Seedlings 1 Hour After Inoculation With *Erysiphe graminis* f. sp *tritici* | w1m1.pk0005.d6 |
| wr1 | Wheat Root From 7 Day Old Seedling | wr1.pk164.h10 |

*These libraries were normalized essentially as described in U.S. Pat. No. 5,482,845, incorporated herein by reference.

pLog value, the greater the likelihood that the cDNA sequence and the BLAST "hit" represent homologous proteins.

Example 3

Characterization of cDNA Clones Encoding Cycloartenol Synthase

The BLASTX search using the EST sequences from clones listed in Table 3 revealed similarity of the polypeptides encoded by the cDNAs to cycloartenol synthase from *Glycyrrhiza glabra* (NCBI General Identifier No. 4589852). Shown in Table 3 are the BLAST results for the sequences of the entire cDNA inserts comprising the indicated cDNA clones ("FIS"), or sequences en coding the entire protein derived from an FIS ("CGS"):

TABLE 3

BLAST Results for Sequences Encoding Polypeptides Homologous to Cycloartenol Synthase

| Clone | Status | BLAST pLog Score 4589852 |
|---|---|---|
| cep7.pk0019.f10 | CGS | >254.00 |
| r1r2.pk0004.f6 | FIS | >254.00 |
| sdp2c.pk008.g6 | CGS | >254.00 |
| wr1.pk164.h10 | FIS | 160.0 |

The data in Table 4 represents a calculation of the percent identity of the amino acid sequences set forth in SEQ ID NOs:2, 4, 6 and 8 and the *Glycyrrhiza glabra* sequence (NCBI General Identifier No. 4589852).

TABLE 4

Percent Identity of Amino Acid Sequences Deduced From the Nucleotide Sequences of cDNA Clones Encoding Polypeptides Homologous to Cycloartenol Synthase

| SEQ ID NO. | Percent Identity to 4589852 |
|---|---|
| 2 | 78.2 |
| 4 | 77.8 |
| 6 | 90.4 |
| 8 | 75.1 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn, a rice, a soybean and a wheat cycloartenol synthase. These sequences represent the first corn, rice, soybean, and wheat sequences encoding cycloartenol synthase.

Example 4

Characterization of cDNA Clones Encoding Squalene Monooxygenase

The BLASTX search using the EST sequences from clones listed in Table 5 revealed similarity of the polypeptides encoded by the cDNAs to squalene monooxygenase from *Panax ginseng* (NCBI General Identifier No. 2804278). Shown in Table 5 are the BLAST results for the sequences of the entire cDNA inserts comprising the indicated cDNA clones ("FIS"), contigs assembled from an FIS and one or more ESTs ("Contig*"), or sequences encoding the entire protein derived from an FIS ("CGS"):

TABLE 5

BLAST Results for Sequences Encoding Polypeptides Homologous to Squalene Monooxygenase

| Clone | Status | BLAST pLog Score 2804278 |
|---|---|---|
| Contig of:<br>csi1n.pk0037.a8<br>p0045.ckdac10r<br>p0083.cldb104r | Contig* | >254.00 |
| Contig of:<br>resc.pk006.o13<br>r10n.pk0031.d7 | Contig* | 161.00 |
| sdp3c.pk003.a5 | CGS | >254.00 |
| w1m1.pk0005.d6 | FIS | >254.00 |

The data in Table 6 represents a calculation of the percent identity of the amino acid sequences set forth in SEQ ID NOs:10, 12, 14 and 16 and the *Panax ginseng* sequence (NCBI General Identifier No. 2804278).

TABLE 6

Percent Identity of Amino Acid Sequences Deduced From the Nucleotide Sequences of cDNA Clones Encoding Polypeptides Homologous to Squalene Monooxygenase

| SEQ ID NO. | Percent Identity to 2804278 |
|---|---|
| 10 | 81.9 |
| 12 | 80.6 |
| 14 | 75.7 |
| 16 | 83.7 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of,a corn, a rice,. a soybean, and a wheat squalene monooxygenase. These sequences represent the first corn, rice, soybean, and wheat sequences encoding squalene monooxygenase.

Example 5

Expression of Chimeric Genes in Monocot Cells

A chimeric gene comprising a cDNA encoding the instant polypeptides in sense orientation with respect to the maize 27 kD zein promoter that is located 5' to the CDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL 1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LHI 32. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment: method (Klein et al. (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 6

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotideshupstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L $CaCl_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/F7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 $\mu$g/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 $\mu$L of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 $\mu$g/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-$\beta$-galactoside, the inducer) can be added to a final concentration of 0.4 mM and incubation can be continued for 3 h at 25°. Cells are then harvested by centrifugation and re-suspended in 50 $\mu$L of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One $\mu$g of protein from the soluble fraction of the culture can be separated by SDS-polyacrylamide gel electrophoresis. Gels can be observed for protein bands migrating at the expected molecular weight.

Example 8

Evaluating Compounds for their Ability to Inhibit the Activity of Enzymes Involved in Squalene Metabolism The polypeptides described herein may be produced using any number of methods known to those skilled in the art.

Such methods include, but are not limited to, expression in bacteria as described in Example 7, or expression in eukaryotic cell culture, in plant a, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instants polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose4B. In an alternate embodiment, a thioredoxin fusion protein may be eluted using dithiothreitol; however, elution may be accomplished using other reagents which interact to displace the thioredoxin from the resin. These reagents include P-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for cycloartenol synthase are presented by Morita et al. (1997) *Biol. Pharm. Bull.* 20:770–775. Assays for squalene monooxygenase are presented by Grieveson et al. (1997) *Anal. Biochem.* 252:19–23.

What is claimed is:

1. An isolated polynucleotide comprising:
   (a) a nucleotide sequence encoding a polypeptide having squalene monooxygenase activity, wherein the amino acid sequence of the polypeptide and the amino acid sequence of SEQ ID NO:14 have at least 90% identity based on the Clustal method of alignment, or
   (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of SEQ ID NO:14 have at least 95% identity based on the Clustal alignment method.

3. The polynucleotide of claim 1, wherein the polypeptide comprises the amino acid sequence of SEQ ID NO:14.

4. The polynucleotide of claim 1, wherein the nucleotide sequence comprise the nucleotide sequence of SEQ ID NO:13.

5. A cell comprising the polynucleotide of claim 1.

6. The cell of claim 5, wherein the cell is selected from the group consisting of a yeast cell, a bacterial cell and a plant cell.

7. A transgenic plant comprising the polynucleotide of claim 1.

8. A method for transforming a cell comprising introducing into a cell the polynucleotide of claim 1.

9. A method for producing a transgenic plant comprising (a) transforming a plant cell with the polynucleotide of claim 1, and (b) regenerating a plant from the transformed plant cell.

10. A chimeric gene comprising the polynucleotide of claim 1 operably linked to at least one regulatory sequence.

11. A vector comprising the polynucleotide of claim 1.

12. A seed comprising the chimeric gene of claim 10.

13. A method for isolating a polypeptide encoded by the polynucleotide of claim 1 comprising isolating the polypeptide from a cell containing a chimeric gene comprising the polynucleotide operably linked to a regulatory sequence.

* * * * *